United States Patent [19]
Ladd

[11] Patent Number: 6,059,814
[45] Date of Patent: *May 9, 2000

[54] FILTER FOR FILTERING FLUID IN A BODILY PASSAGEWAY

[75] Inventor: William Gregory Ladd, Williamsport, Tenn.

[73] Assignee: Medtronic Ave., Inc., Santa Rosa, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/921,345

[22] Filed: Aug. 29, 1997

Related U.S. Application Data

[60] Provisional application No. 60/084,197, Jun. 2, 1997.

[51] Int. Cl.[7] .................................................. A61B 17/00
[52] U.S. Cl. ............................................................ 606/200
[58] Field of Search .................................... 606/200, 191, 606/194, 195, 198, 192, 159; 623/1, 11, 12; 604/104, 174, 106–109, 105

[56] References Cited

U.S. PATENT DOCUMENTS

| | | |
|---|---|---|
| 4,425,908 | 1/1984 | Simon . |
| 4,790,812 | 12/1988 | Hawkins, Jr. et al. . |
| 4,873,978 | 10/1989 | Ginsburg . |
| 4,926,858 | 5/1990 | Gifford, III et al. . |
| 5,071,407 | 12/1991 | Termin et al. . |
| 5,329,942 | 7/1994 | Gunther et al. . |
| 5,421,832 | 6/1995 | Lefebvre . |
| 5,549,626 | 8/1996 | Miller et al. . |
| 5,730,726 | 3/1998 | Klingenstein ........................... 604/105 |
| 5,814,064 | 9/1998 | Daniel et al. . |
| 5,827,324 | 10/1998 | Cassell et al. . |

FOREIGN PATENT DOCUMENTS

| | | |
|---|---|---|
| PCT/US95/ 08613 | 7/1995 | WIPO . |
| WO 98/33443 | 8/1998 | WIPO ........................... A61B 17/22 |

*Primary Examiner*—Michael Buiz
*Assistant Examiner*—Vikki Trinh
*Attorney, Agent, or Firm*—Richard L. Klein; Catherine C. Maresh

[57] ABSTRACT

A filter for filtering micro-emboli from a patient's blood during an angioplasty procedure is disclosed which comprises a plurality of curved wires connected to a rod between a first connector fixed with respect to the rod and a second connector slidingly mounted on the rod. Two layers of filter material are connected to opposite sides of the wires, and each layer includes perforations which are offset from the perforations in the other layer. When the rod and the wires are disposed within a catheter, the inner wall of the catheter compresses the wires toward the rod and when the rod is extended from the catheter, the wires resume their curved shape and pull the sliding connector along the rod toward the fixed connector.

12 Claims, 4 Drawing Sheets

FILTER FOR FILTERING FLUID IN A BODILY PASSAGEWAY

This application claims the benefit of the filing date of U.S. Provisional Application Ser. No. 60/084,197, which was filed on Jun. 2, 1997.

The present application is directed toward a filter, and more specifically, toward a filter for use during a catheterization procedure for filtering blood downstream of the procedure site.

BACKGROUND OF THE INVENTION

Arteriosclerosis is a condition in which plaques develop on the inner walls of blood vessels and restrict the flow of blood therethrough. Organs downstream of this constriction can be starved of oxygen, and the heart must work harder to pump blood through a circulatory system that includes such blockages. When the blockage occurs in the coronary arteries which feed the heart, a heart attack can result. Similarly, blockages in the carotid arteries can restrict the flow of blood to the brain with obvious negative consequences.

These blockages are often found in locations that are difficult to access. For example, the coronary arteries are protected by the rib cage and the some portions of the carotid arteries. At one time, major surgery was required to reach these locations. However, several methods have been developed for treating plaques in these areas, which methods involve the insertion of a catheter into a patient's blood vessel at a location that is easy to reach, and guiding the catheter through the vessel toward the blockage. A variety of tools can be passed through the catheter to treat the blockage, such as lasers or other cutting tools. However one of the more common tools is a balloon which is placed in the constricted area of the vessel and inflated once or a number of times in order to push the plaque back against the arterial wall to open the artery. This procedure is called balloon angioplasty and is a common treatment for arteriosclerosis today.

In order to get a balloon to the location of the blockage, a catheter must be placed into a patient's artery. This is done by inserting a needle into an easily accessible artery and threading a guide wire through the needle and into the patient's artery. The needle is withdrawn over this guide wire and an arterial sheath is place over the needle and into the artery to protect the artery and surrounding tissue during the procedure. A guiding catheter is placed over the guide wire and maneuvered through the artery to a position near the site of the blockage. When the end of the guiding catheter arrives at a location near the blockage, the guide wire is removed, and the catheter is flushed with saline and anchored in place in a suitable manner. A balloon catheter, having an associated guide wire is then inserted into the guiding catheter and pushed through the catheter, out of the distal end of the catheter, and guided to the site of the blockage. The guide wire is pushed past the blockage and the balloon is positioned within the blockage and inflated to compress the buildup in the artery. When the procedure is complete, the balloon catheter is removed from the guiding catheter and then the guiding catheter is removed as well. This procedure has had a high success rate and is the preferred method for treating certain types of blockages.

One of the dangers associated with this procedure is that a part of the plaque could break off and enter the patient's blood stream during treatment. While no part of the plaque is actually cut away during a balloon angioplasty procedure, small pieces of plaque known as micro-emboli can and do sometimes break free. These materials are often too large to pass easily through the body's capillaries and can become lodged therein and block the flow of blood. If the blockage occurs in the brain or the lungs, it can be harmful or even fatal. Therefore, a variety of techniques are used to stop these particles before they travel too far.

Heretofore, various filters have been used to trap these particles. Some, such as the filter disclosed in U.S. Pat. No. 4,873,978 to Ginsburg comprise a wire mesh for straining objects from the bloodstream. However, this strainer must be inserted into a blood vessel through its own opening, downstream from the treatment site and separate from the opening used for the balloon catheter or similar device. This makes this filter difficult to use and creates additional discomfort for the patient. Others, such as the filter shown in U.S. Pat. No. 4,425,908 to Simon are intended to be permanently attached to the inner wall of a blood vessel. However, it is often desirable to remove the filter after a procedure is complete, and this would not be practicable using the Simon filter.. In addition, the wire mesh strainers disclosed in these patents might be capable of stopping relatively large pieces of material, such as those generated when a plaque is severed from an arterial wall by a cutting instrument, but are not suitable for stopping the micro-emboli that can occur during a balloon angioplasty procedure. Neither these nor any other known devices provide a simple and effective option for dealing with such micro-emboli while at the same time functioning to block any larger pieces of material that might break free. It would therefore be desirable to provide a blood filter for trapping micro-emboli that could be deployed immediately before a procedure was commenced and removed shortly thereafter and which could be inserted and removed through the same catheter used in connection with the procedure.

SUMMARY OF THE INVENTION

The present invention overcomes these and other problems by providing a compact filter for use alone or as part of an apparatus for performing a balloon angioplasty. The filter comprises a rod slidingly housed within a catheter, and a plurality of curved, flexible wires longitudinally disposed along the rod and connected thereto at two spaced apart locations. A portion of filter material is supported by the wires. When the rod is inside the catheter, the wires are held in close proximity to the rod by the walls of the catheter. When the rod is extended from the catheter, the wires resume their preformed, curved shape and curve away from the rod. This stretches the filter material across the passageway to trap any plaques or clots that are present. When the need for filtration is ended, the rod is pulled back into the catheter. This process compresses the wires against the rod and closes the filter material around any trapped materials so that they can be removed from the body.

In a preferred embodiment of the invention, the flexible wires are attached to two connectors on the outer surface of the rod. The connectors are ring-shaped and the wires are evenly distributed about the circumference of the rings. The connector closest to the distal end of the rod (the end inside the patient's body) is slidably connected to the rod while the proximal connector is fixed. The wires are preformed in a curved shape such that when unbiased by the walls of the catheter, they extend from the proximal connector through an arc that takes them away from the rod and then back toward the distal connector where they are also attached. The volume defined by the wires is generally ovoid, and the largest diameter of the volume perpendicular to the axis of the rod is selected to be about equal to the diameter of the blood vessel in which the filter is to be used. Because the wires are flexible, and because the distal connector can slide relative to the rod, when the rod is pulled into a catheter, the wires are compressed toward the rod and the distal connector is slid along the rod away from the proximal connector. When the rod is pushed out of the catheter, the distal connector slides toward the proximal connector and the wires resume their preformed shape.

A filter element is attached to the wires to trap material that comes loose from the arterial walls during a procedure. In the preferred embodiment, two layers of a biocompatible material, such as Gortex brand fabric, are used as the filter element with one layer attached to the side of the wires facing the rod and the other attached to the opposite side so that the wires are sandwiched in-between the two layers. The material extends from the distal connector toward the midpoint of the wires or even slightly further toward the proximal connector. Each layer includes small perforations to allow fluids to pass while trapping even very small emboli. The perforations on the inner sheet are offset from those on the outer sheet to better trap and retain emboli.. The material is pulled inwardly toward the rod by the wires when the rod is retracted into a catheter and is thin enough to fold easily.

The filter can be inserted by itself, but preferably, it is carried on the same rod used to hold a balloon for a balloon angioplasty procedure. In use, therefore, the balloon catheter will be guided through an arterial narrowing so that its distal end extends beyond the narrowing and so that the balloon is positioned within the narrowing. The rod is then extended from the catheter to push out the filter a distance of about 1 millimeter. After the balloon has been inflated and deflated to enlarge the passageway, the rod and filter are pulled back into the catheter and the catheter is removed from the body.

The filter also includes safety features to prevent parts of the filter itself from breaking off of the rod. A stop is included on the distal end of the rod which will prevent the slidable connector ring from sliding all the way off of the rod in the unlikely event that the wires holding it to the proximal connector should be broken. In addition, a safety wire is attached between the proximal connector and the distal connector, as well as to the midpoint of the rod therebetween. This wire limits the movement of the distal connector in both directions along the rod. By preventing the distal connector from moving too far in a distal direction, it prevents the other wires extending between the connectors from being stressed. By preventing the distal connector from moving too far in the proximal direction, it limits the diameter of the ovoid volume defined by the curved wires so as not to damage the vessel walls that surround the filter.

It is therefore a primary object of the present invention to provide an apparatus for filtering a fluid in a bodily passageway.

It is another object of the present invention to provide a filtering device for filtering blood flowing through a blood vessel.

It is a further object of the present invention to provide a collapsible filtering device which can be passed through a narrowing in a blood vessel and then expanded to its functional size on the other side of the narrowing.

It is yet another object of the present invention to provide a filtering device which can be inserted into a blood vessel through a catheter.

It is yet a further object of the present invention to provide a filtering device that can be attached to an instrument used during an angioplasty procedure.

It is still another object of the present invention to provide a filter suitable for trapping both large and small particles of material in the bloodstream.

It is still a further object of the present invention to provide a filtering device that can be deployed and retracted in a simple manner from a remote location.

It is yet another object of the present invention to provide a filter for use in conjunction with a catheter which filter is shifted between functional and storage configurations by sliding it into and out of the catheter.

It is another object of the present invention to provide a filter that can be deployed and retracted by sliding the filter support relative to a tubular member such as a catheter.

It is yet another object of the present invention to provide a filtering apparatus that includes safety features to help prevent portions of the apparatus from separating from the apparatus.

BRIEF DESCRIPTION OF THE DRAWINGS

These and other objects will become evident from a reading and understanding of the following detailed description of a preferred embodiment of the invention together with the following drawings of which.

DETAILED DESCRIPTION OF THE PREFERRED EMBODIMENT

Figure 1:
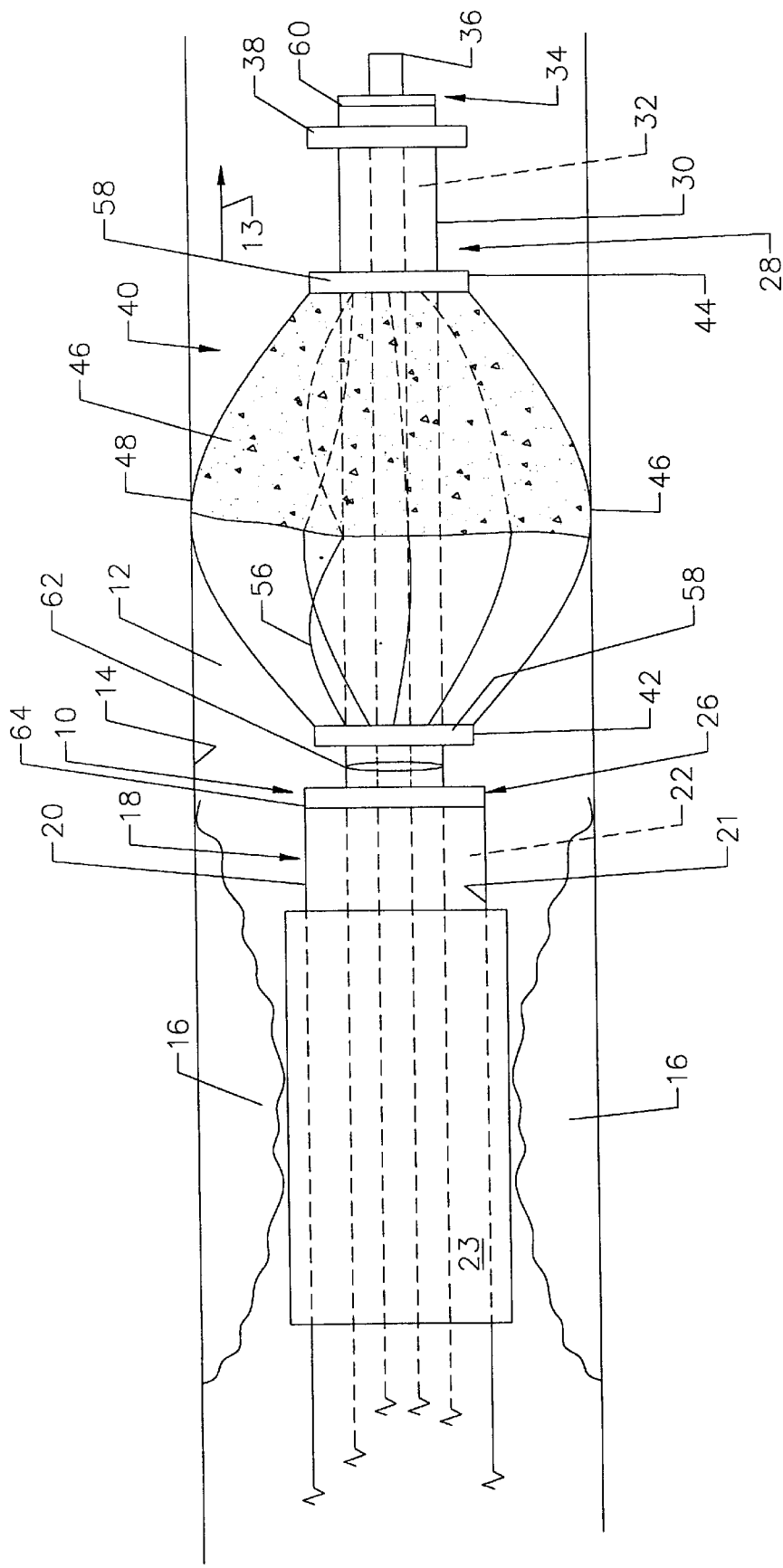
FIG. 1 is an elevational view of a filter apparatus according to the present invention showing the filter in its fully open condition extending out of a balloon catheter.
Figure 2:
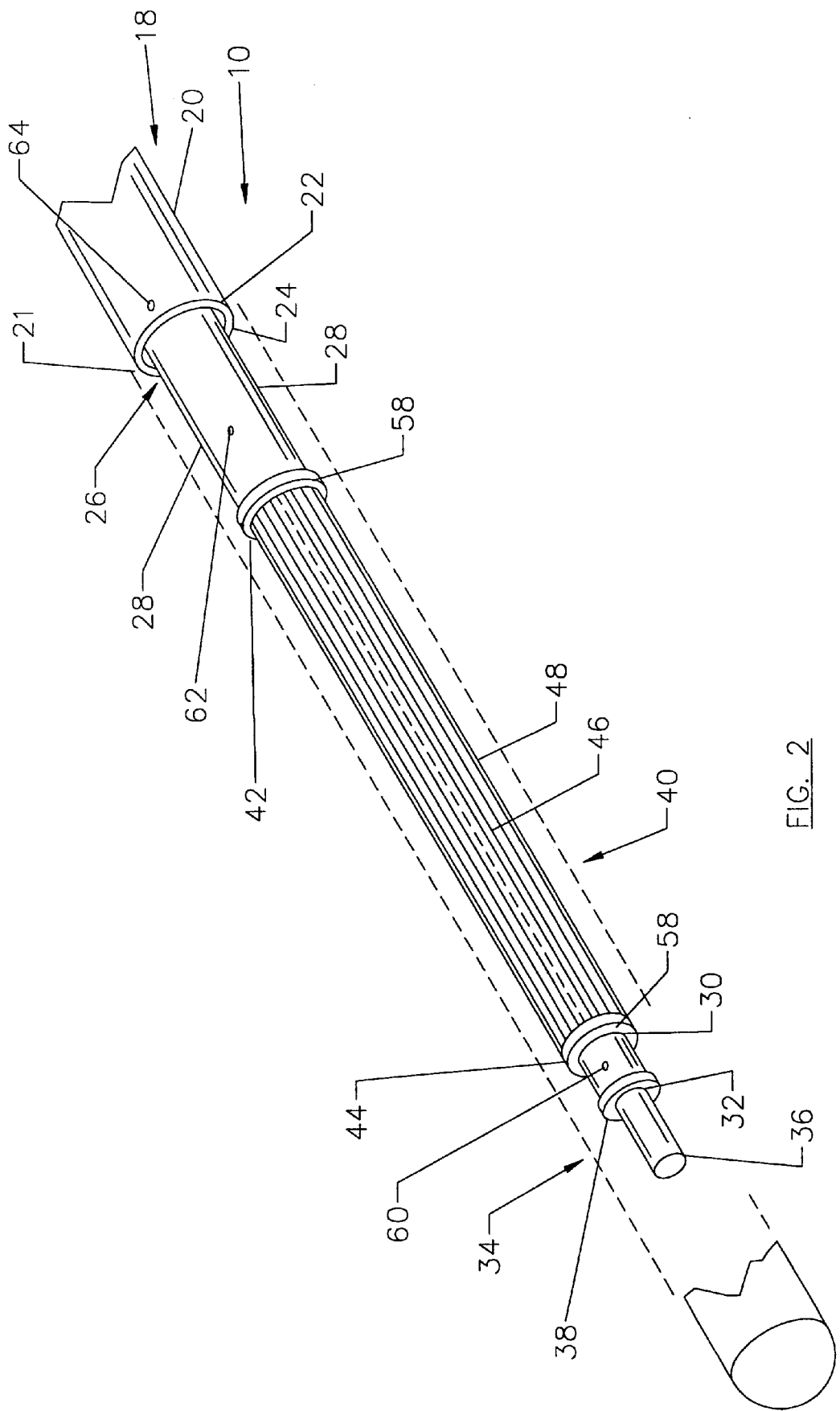
FIG. 2 is a pictorial view, partly in section, of the filter of FIG. 1 collapsed within a catheter.
Figure 3:
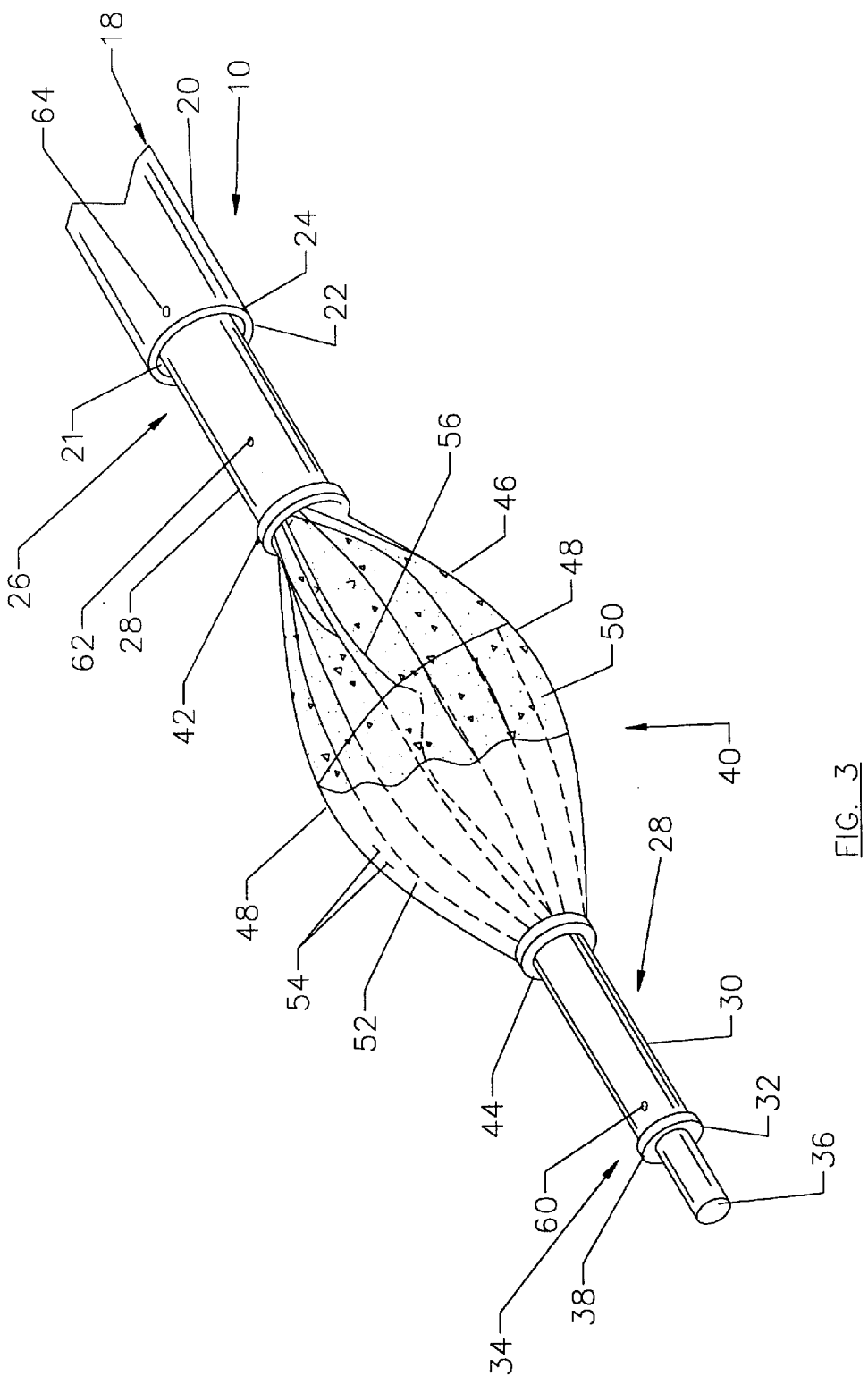
FIG. 3 is a pictorial view, partly in section, of the subject filter extending part of the way out of a catheter; and, FIG. 4 is a pictorial view, partly in section, of the subject filter in its fully open condition.
Figure 4:
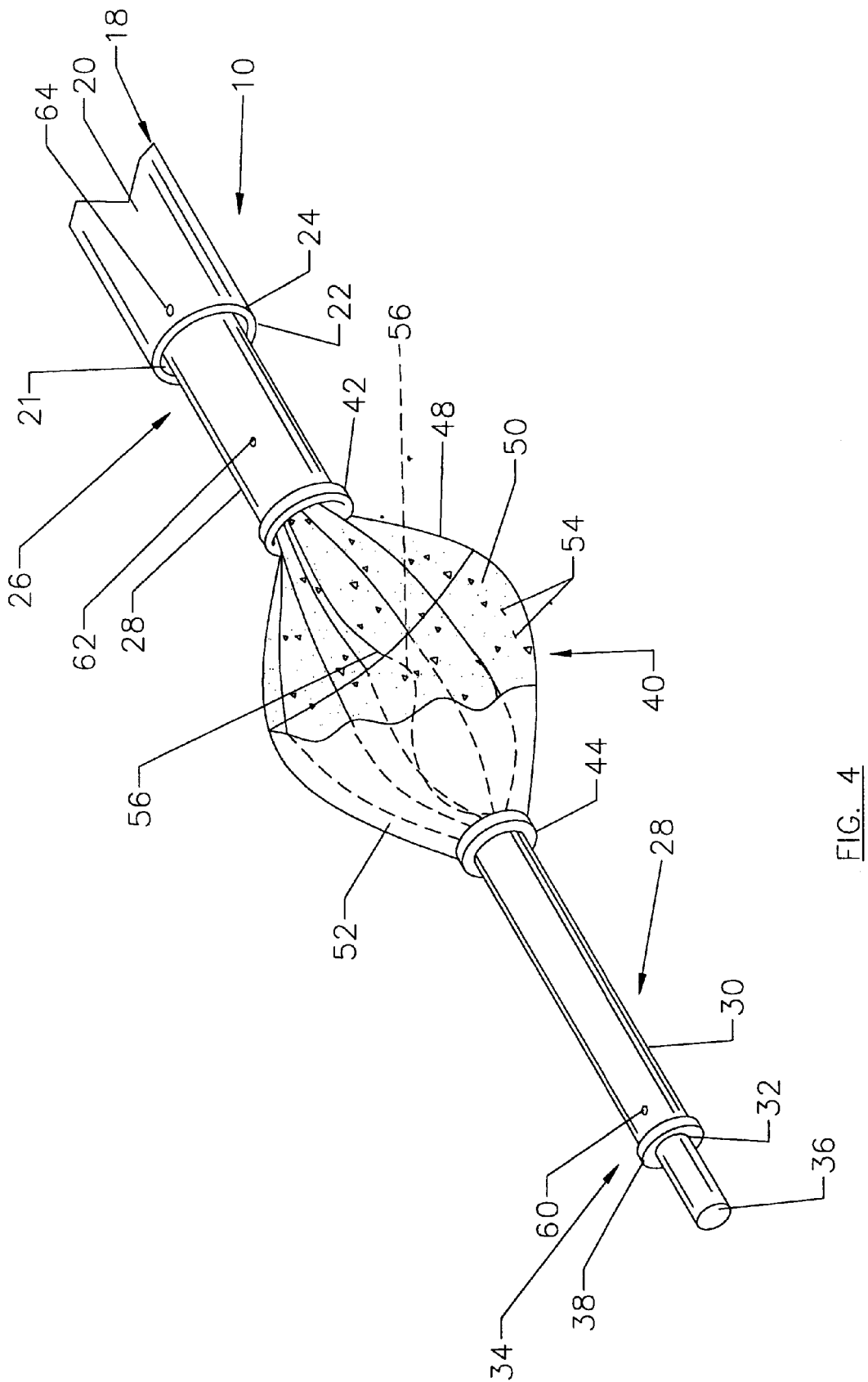

Referring now to the drawings, wherein the showings are for the purpose of illustrating a preferred embodiment of the subject invention only and not for the purpose of limiting same, FIG. 1 shows a balloon catheter assembly designated generally by the numeral 10 positioned within an artery 12 having walls 14 wherein blood flows in the direction of arrow 15. Plaques 16 on walls 14 decrease the diameter of artery 12, and the purpose of the angioplasty procedure is to compress plaques 16 against walls 14 to increase the blood flow through artery 12. Catheter assembly 10 comprises a balloon catheter 18 having an outer wall 20, an inner wall 21, a lumen 22 and a distal end wall 24 at its distal end 26. (In this description, the term "distal" refers to the end of the catheter assembly deep within the patient's body and the term "proximal" refers to the end of the assembly outside of the patient's body). A balloon 26 is connected to outer wall 20 of catheter 18 and is equipped with suitable inflation means (not shown) to cause the balloon to expand against plaques 16. The use of a balloon for this purpose is well known and the mechanism for inflating and deflating the balloon does not comprise a part of the present invention. A rod 28, preferably made from Nitinol or titanium, is disposed within lumen 22 for sliding movement with respect to catheter 18 and includes an outer wall 30, a lumen 32, and a distal end 34. The rod has an outer diameter of about 0.020 millimeters and an inner diameter of about 0.018 millimeters. A guide wire 36 is housed within lumen 32 for sliding movement with respect to rod 28. Rod 28 includes a stop 38 mounted on outer wall 30 near distal end 34 and a filter assembly designated generally by the numeral 40 mounted on outer wall 30 proximally of stop 38.

Filter assembly 40 comprises a proximal ring connector 42 and a distal ring connector 44 located between proximal connector 42 and stop 38. Each ring has an outer diameter of about 0.021 and an inner diameter of about 0.020 and is about 0.005 millimeters thick. Proximal ring 42 is fixedly connected to outer wall 30 while distal ring 44 is free to slide longitudinally along the outer wall of rod 28. Twelve flexible wires 46 are connected between rings 42 and 44 such as by welding them to the connectors. This number of wires has been found to provide satisfactory performance, but a greater or lesser number of wires could be used if desired. These wires are preformed to have a curved shape so that when connected between connectors 42 and 44 they arc outwardly from the rod a distance sufficient to bring them into contact with the wall of the vessel in which the filter is used. More specifically, the wires are curved so that the diameter of a section taken perpendicular to rod 28 and through a midpoint 48 of the wires is approximately equal to or slightly larger than the diameter of artery 12. In this manner, it is assured that the midpoints 48 of the wires will be pressed firmly against the wall 14 of artery 12 when the filter is deployed as will be described hereinafter. These wires are uniformly spaced about the circumferences of rings 42, 44, extend generally parallel to each other, and are preferably made from a 0.002 mm titanium wire. When in its operative position, filter assembly 40 is approximately 4 millimeters long from ring 42 to ring 44.

Filter assembly 40 also includes a first layer of filter material 50 secured to wires 46 on the side of wires 46 facing rod 28 and a second layer of filter material 52 secured to wires 46 on the side of the wires opposite from first layer 50. Layers 50 and 52 extend from distal ring 44 to approximately midpoints 48 of wires 46 or a point slightly closer to proximal ring 42 than midpoint 48. The preferred material for forming these filter layers is Gortex brand fabric because of its ability to withstand the conditions present in the bloodstream and because it is well tolerated by the body. Other similar materials could readily be substituted therefor. Each layer 50, 52 includes a plurality of perforations 54 which perforations are evenly distributed over the surface of each sheet. The sheets are arranged, however, so that the perforations in the sheets are not aligned. These perforations allow for improved blood flow through the filter, while still allowing the filter to trap and retain very small microemboli.

Rings 42 and 44 have an outer diameter less than the inner diameter of balloon catheter 18 and slide freely within lumen 22. The diameter of filter assembly 40 at midpoints 48 is substantially greater than the inner diameter of catheter 18, and, except in the immediate vicinity of rings 42, 44, the cross section of wires 46 normal to rod 28 is also greater than the inner diameter of the catheter. Therefore, when rod 28 is drawn into catheter 18, proximal ring 42 passes into lumen 22 but wires 46 come into contact with distal end wall 24. Because the wires are flexible, however, they are compressed toward rod 28 by end wall 24 as the filter assembly 40 moves into lumen 22. As the wires are forced toward rod 28, they push distal ring 44 away from proximal ring 42. Distal ring 44 continues to slide in this direction until midpoints 48 of wires 46 are drawn past distal end wall 24. After this point, the remaining portion of filter assembly 40 can be drawn into lumen 22 while ring 44 remains in essentially the same position. Stop 38 has an outer diameter smaller than the inner diameter of catheter 18 and also passes freely into the catheter along with rod 28. These steps are reversed when rod 28 is pushed out of catheter 18. Stop 38 and distal ring 44 exit past distal end wall 24 of catheter 18 and wires 46 continue to be held in the orientation they assumed when inside the catheter, generally parallel to rod 28 and generally evenly spaced therefrom along their entire lengths. As midpoints 48 exit the catheter, wires 46 begin to return to their preformed, curved shape and spread away from rod 28 in all directions. This in turn pulls distal ring 44 back toward proximal ring 42 until proximal ring 42 has moved outside of the catheter.

Catheter assembly 10 also includes a number of safety features to ensure that, even if the device is damaged during use, parts thereof will not break off and enter the bloodstream. First, wires 46 are all made from titanium which does not react with water or the chemicals present in the blood stream. In addition, titanium has great strength for per unit weight which reduces the chance that the wires will break during normal use. Wires 46 are each fastened to both rings by welds and therefore both ends of the wires will remain attached to a structure even if a wire breaks. In the unlikely event that all of wires 46 break, or that they all become detached from distal ring 44, stop 38 will prevent ring 44 from sliding off of rod 28 and into the bloodstream. Finally, a safety wire 56 is connected between proximal ring 42 and distal ring 44 and also welded to rod 28 at a central point therebetween. Wire 56 limits the range of movement of distal ring 44 and is fully extended along rod 28 when wires 46 are pressed against rod 46. This wire provide added protection to retain distal ring 44 on rod 28. Wire 56 also provides a biasing force to help prevent distal ring 44 from coming too close to proximal ring 42. These safety features help to ensure that the subject device functions properly during use.

To use the subject filter, rod 28 is inserted into lumen 22 of catheter 18 and positioned so that filter assembly 40 is located generally interiorly of balloon 23. Guide wire 36 is inserted into lumen 32 to allow balloon catheter 18 to be steered through a patient's blood vessels. The entire assembly is coated with heparin to reduce clot formation during the procedure. A needle next inserted into an easily accessible artery and a guide wire (not shown) is threaded through the needle and into the patient's artery. The needle is withdrawn over this guide wire and an arterial sheath is place over the needle and into the artery to protect the artery and surrounding tissue during the procedure. A guiding catheter, also coated with heparin, (not shown) is placed over the guide wire and maneuvered through the artery to a position near the site of the blockage. At this point the guide wire is removed and the catheter is flushed with saline solution. Balloon catheter 18 with filter assembly 40 housed within, is next inserted through the guiding catheter and out of the distal end thereof. From this point, guide wire 36, which extends beyond rod 28 and out of catheter 18, is used to steer the catheter to the site of the blockage. The fact that distal ring 44 is slidingly attached to rod 28 makes it easier to navigate the tortuous pathway through the bloodstream to the site of the blockage or narrowing. When ring 44 contacts the wall of an artery, for example, it can easily slide out of the way and this reduces the need for backing up and repositioning the catheter during the insertion process. Guide wire 36 is passed through the narrowed part of the artery and balloon 23 is positioned in this narrowing. Rod 28 is then extended from catheter 18 so that proximal ring 42 is spaced about 1 millimeter distally of distal end wall 24. Wires 46 have been chosen based on the size of artery 12 and press firmly against wall 14 of the artery which in turn holds filter elements 50 and 52 against the wall.

To help locate the filter assembly during an angiographic procedure, radiopaque markers 58 are placed on both the proximal and distal rings. Additional radiopaque markers 60 and 62 are placed on shaft 28 and another marker 64 is placed at the end of catheter 18. Marker 60 is located at the end of shaft 18 and, when aligned with marker 64, shows that the distal end of rod 28 is at the end of catheter 18. The second rod marker 62 is located proximally of filter assembly 40, and when marker 62 is aligned with marker 64 indicates that the filter assembly has exited the catheter.

The balloon is inflated once or a number of times to compress plaque 16 against the arterial wall. During this procedure, blood is flowing past the plaque and balloon and micro-emboli which form will flow toward filter apparatus 40 and be trapped therein. When the compression of the plaques is complete, rod 28 is pulled back into catheter 18 along with any particles trapped by the filter. Using standard techniques, it is also possible to leave the filter in place temporarily while the balloon catheter is removed and replaced with a stent, a stent catheter balloon, or a balloon of a different size. To do this, an exchange length wire of approximately 300 centimeters must be used. This requires that shaft 28 be of this exchange length as well. When this procedure is complete, the filter is withdrawn into the lumen of whichever catheter is in place.

The invention has been described herein in terms of a preferred embodiment and many changes and modifications will become obvious to the skilled practitioner upon a reading and understanding of the foregoing description and an examination of the drawings. It is intended that all of these modifications be included within the scope of this invention to the extent that they are defined by the several claims appended hereto.

I claim:

1. A filter apparatus for filtering blood downstream of an arterial narrowing during a procedure to widen the arterial narrowing, comprising:

a catheter having an inner wall and an open end;

a hollow rod having an outer surface and a first end and a second end slidingly disposed within said catheter;

a guide wire disposed within said hollow rod;

a first ring member fixedly connected to said outer surface of said rod;

a second ring member slidingly connected to said outer surface of said rod between said first ring member and said rod second end;

a plurality of flexible wires preformed into a curved shape and having first ends connected to said first ring member and second ends connected to said second ring member;

a first sheet of filter material having perforations and connected to said plurality of wires between said rod and said wires, said first sheet having a length less than the length of said plurality of wires;

a second sheet of filter material having perforations and connected to said plurality of wires, said second sheet perforations being offset from said first sheet perforations;

a safety wire connected between said first ring member and said second ring member and to said rod; and, a safety stop connected to said rod between said second ring member and said rod second end;

whereby said plurality of wires are compressed by said catheter inner wall when said rod is inside of said catheter and whereby said plurality of wires expand to assume their preformed shape and contact the wall of said artery when said rod second end and said wires are extended from said catheter.

2. A filter apparatus comprising:

a rod receivable over a guidewire, a catheter slidingly disposed over said rod;

a flexible frame having a first end and a second end, a first connector for connecting said first end of said flexible frame to said rod;

a second connector for connecting said second end of said flexible frame to said rod;

a stop mounted on said rod between said second connector and a distal end of said rod for preventing said second connector from sliding off of said rod distal end; and a filter material connected to said flexible frame whereby extending said rod out of said catheter allows said flexible frame and said filter material to expand from said rod and drawing said rod into said catheter compresses said flexible frame and filter material toward said rod.

3. A filter apparatus comprising:

a rod receivable over a guidewire, a catheter slidingly disposed over said rod;

a flexible frame having a first end and a second end, a first connector for connecting said first end of said flexible frame to said rod;

a second connector for connecting said second end of said flexible frame to said rod;

a safety wire connected between said first connector and said second connector and to a point on said rod there between for limiting the movement of said second connector relative to said rod; and a filter material connected to said flexible frame whereby extending said rod out of said catheter allows said flexible frame and said filter material to expand from said rod and drawing said rod into said catheter compresses said flexible frame and filter material toward said rod.

4. A vascular filter apparatus comprising:

a core wire having proximal and distal ends and a lumen;

a filter concentrically arranged around said core wire, said filter having proximal and distal ends, the distal end of the filter being attached to the core wire adjacent its distal end and the proximal end of the filter being attached to the core wire wherein the proximal end of the filter is slidably attached to the core wire by a radiopaque marker or crimp band and the distal end of the filter is fixedly attached to the core wire by a radiopaque marker or crimp band; and a sheath concentrically arranged around the core wire and having proximal and distal ends, the distal end of the sheath having a lumen of sufficient diameter to slide over the proximal portion of the filter.

5. A vascular filter apparatus comprising:

a core wire having proximal and distal ends and a lumen;

a filter concentrically arranged around said core wire, said filter having proximal and distal ends, the distal end of the filter being attached to the core wire adjacent its distal end and the proximal end of the filter being attached to the core wire wherein the proximal end of the filter is fixedly attached to the core wire by a radiopaque marker or crimp band and the distal end of the filter is slidably attached to the core wire by a radiopaque marker or crimp band; and a sheath concentrically arranged around the core wire and having proximal and distal ends, the distal end of the sheath having a lumen of sufficient diameter to slide over the proximal portion of the filter.

6. An apparatus for filtering fluid in a bodily passageway comprising:

a hollow tube having an open end;

a rod having a first end and a second end slidingly disposed within said tube;

a plurality of flexible strands preformed into a predetermined shape, each having a first end fixed to said rod at a first point and a second end moveably connected to said rod between said first point and said rod second end;

a first connector connecting said first ends of said plurality of strands to said rod said first connector fixed on said rod and a second connector connecting said second ends of said plurality of strands to said rod, said second connector moveable on said rod, such that drawing said rod into said tube and compressing said plurality of strands causes said second connector to move toward said rod second end and away from said first connector;

a stop mounted on said rod between said second connector and said rod second end for preventing said second connector from sliding off of said rod end;

a filter material made from a substantially flexible material connected to said plurality of strands, whereby extending said rod out of the open end of the hollow tube allows the plurality of strands to expand, which expands the filter material, and drawing said rod into said tube compresses the plurality of flexible strands toward the rod.

7. An apparatus for filtering fluid in a bodily passageway comprising:

a hollow tube having an open end;

a rod having a first end and a second end slidingly disposed within said tube;

a plurality of flexible strands preformed into a predetermined shape, each having a first end fixed to said rod at a first point and a second end moveably connected to said rod between said first point and said rod second end;

a first connector connecting said first ends of said plurality of strands to said rod said first connector fixed on said rod and a second connector connecting said second ends of said plurality of strands to said rod, said second connector moveable on said rod, such that drawing said rod into said tube and compressing said plurality of strands causes said second connector to move toward said rod second end and away from said first connector;

a safety wire connected between said first connector and said second connector and to a point on said rod there between for limiting the movement of said second connector relative to said rod;

a filter material made from a substantially flexible material connected to said plurality of strands, whereby extending said rod out of the open end of the hollow tube allows the plurality of strands to expand, which expands the filter material, and drawing said rod into said tube compresses the plurality of flexible strands toward the rod.

8. A filter apparatus comprising:

a rod receivable over a guidewire;

a catheter slidingly disposed over said rod;

a flexible frame having a first end and a second end;

a first connector for connecting said first end of said flexible frame to said rod;

a second connector for connecting said second end of said flexible frame to said rod;

a stop on said rod between said second connector and a distal end of said rod for preventing said second connector from sliding off of said rod distal end; and a filter material connected to said flexible frame whereby extending said rod out of said catheter allows said flexible frame and said filter material to expand from said rod and drawing said rod into said catheter compresses said flexible frame and filter material toward said rod.

9. A vascular filter apparatus comprising:

a core wire having proximal and distal ends and a lumen;

a filter concentrically arranged around said core wire, said filter having proximal and distal ends, the distal end of the filter being attached to the core wire adjacent its distal end and the proximal end of the filter being attached to the core wire wherein the proximal end of the filter is slidably attached to the core wire by a radiopaque marker or crimp band; and a sheath concentrically arranged around the core wire and having proximal and distal ends, the distal end of the sheath having a lumen of sufficient diameter to slide over the proximal portion of the filter.

10. A vascular filter apparatus comprising:

a core wire having proximal and distal ends and a lumen;

a filter concentrically arranged around said core wire, said filter having proximal and distal ends, the distal end of the filter being attached to the core wire adjacent its distal end and the proximal end of the filter being attached to the core wire wherein the distal end of the filter is fixedly attached to the core wire by a radiopaque marker or crimp band; and a sheath concentrically arranged around the core wire and having proximal and distal ends, the distal end of the sheath having a lumen of sufficient diameter to slide over the proximal portion of the filter.

11. A vascular filter apparatus comprising:

a core wire having proximal and distal ends and a lumen;

a filter concentrically arranged around said core wire, said filter having proximal and distal ends, the distal end of the filter being attached to the core wire adjacent its distal end and the proximal end of the filter being attached to the core wire wherein the proximal end of the filter is fixedly attached to the core wire by a radiopaque marker or crimp band; and a sheath concentrically arranged around the core wire and having proximal and distal ends, the distal end of the sheath having a lumen of sufficient diameter to slide over the proximal portion of the filter.

12. A vascular filter apparatus comprising:

a core wire having proximal and distal ends and a lumen;

a filter concentrically arranged around said core wire, said filter having proximal and distal ends, the distal end of the filter being attached to the core wire adjacent its distal end and the proximal end of the filter being attached to the core wire wherein the distal end of the filter is slidably attached to the core wire by a radiopaque marker or crimp band; and a sheath concentrically arranged around the core wire and having proximal and distal ends, the distal end of the sheath having a lumen of sufficient diameter to slide over the proximal portion of the filter.

* * * * *